United States Patent
Chu et al.

(10) Patent No.: US 12,318,372 B2
(45) Date of Patent: Jun. 3, 2025

(54) FORMULATIONS WITH ENHANCED SN-38 SOLUBILITY AND ORAL ABSORPTION

(71) Applicant: TaiRx Inc., Taipei (TW)

(72) Inventors: Yi-Wen Chu, New Taipei (TW); Du-Shieng Chien, Guilford, CT (US)

(73) Assignee: TAIRX, INC., Taipei (TW)

( * ) Notice: Subject to any disclaimer, the term of this patent is extended or adjusted under 35 U.S.C. 154(b) by 0 days.

(21) Appl. No.: 17/882,458

(22) Filed: Aug. 5, 2022

(65) Prior Publication Data

US 2023/0086405 A1   Mar. 23, 2023

Related U.S. Application Data

(60) Provisional application No. 63/240,990, filed on Sep. 5, 2021.

(51) Int. Cl.
| | | |
|---|---|---|
| *A61K 31/4375* | (2006.01) | |
| *A61K 47/14* | (2017.01) | |
| *A61K 47/22* | (2006.01) | |
| *A61P 35/00* | (2006.01) | |

(52) U.S. Cl.
CPC .......... *A61K 31/4375* (2013.01); *A61K 47/14* (2013.01); *A61K 47/22* (2013.01); *A61P 35/00* (2018.01)

(58) Field of Classification Search
CPC .... A61K 31/4375; A61K 47/14; A61K 47/22; A61K 47/34; A61K 47/38; A61K 9/06; A61K 9/4858; A61P 35/00; G06F 16/328; G06F 16/9024
See application file for complete search history.

(56) References Cited

U.S. PATENT DOCUMENTS

| | | | | |
|---|---|---|---|---|
| 5,100,567 A | * | 3/1992 | Naae | C09K 8/514 507/935 |
| 8,026,286 B2 | * | 9/2011 | Curatolo | A61P 29/00 424/468 |
| 2005/0267140 A1 | | 12/2005 | Miller et al. | |
| 2007/0254905 A1 | | 11/2007 | Seo et al. | |

FOREIGN PATENT DOCUMENTS

| | | | | |
|---|---|---|---|---|
| CN | 100464785 C | | 3/2009 | |
| WO | WO-2006049447 A1 | * | 5/2006 | ........... A61K 31/475 |
| WO | WO-2019173526 A1 | * | 9/2019 | ............. A61K 31/05 |

OTHER PUBLICATIONS

PCCA Blog ("Choosing an Appropriate Gelling Agent for Your Compounded Preparation" Apr. 28, 2021, (Year: 2021).*
Odisha ("World Journal of Pharmaceutical Research" vol. 7, Issue 9, 316-323, Apr. 2018. Conference Article ISSN 2277-7105), (Year: 2018).*
Huntsman (https://monsonco.com/wp-content/uploads/2019/08/Propylene-Glycol-Industrial.-TDS.-REC-12.5.2019.pdf) accessed on Nov. 12, 2024 (Year: 2024).*
https://www.google.com/search?q=pecentage+of+water+in+n-methyl+pyrrolidone&rlz=1C1GCEA_enUS1031US1031&oq=pecentage+of+water+in+n-methyl+pyrrolidone&gs_lcrp=EgZjaHJvbWUyBgg AEEUYOTIJCAEQIRgKGKABMgkIAhAhGAoYoAEyCQgDECE YChigATIJCAQQIRgKGKABMgkIBRAhGAoYoAEyBwgGECE YqwlyBwgHECEY (Year: 2024).*
PCT/US 22/39586 International Search Report dated Nov. 3, 2022.
PCT/US 22/39586 Written Opinion of the Internatoinal Searching Authority dated Nov. 3, 2022.
Rowinsky et al. "Phase I and Pharmacological Study of the Novel Topoisomerase I Inhibitor 7-Ethyl-10-[4-(1-piperidino)-1-piperidino] carbonyloxy camptothecin (CPT-11) Administered as a Ninety-Minute Infusion Every 3 Weeks" Cancer Research 54, 427-436, Jan. 15, 1994.

* cited by examiner

*Primary Examiner* — Jean P Cornet
(74) *Attorney, Agent, or Firm* — Hsiu-Ming Saunders; IPC INTELLECTUAL PROPERTY CONNECTIONS, INC.

(57) ABSTRACT

Formulations with enhanced SN-38 solubility and oral absorption. In one embodiment, a formulation or a pharmaceutical composition comprises (a) 7-Ethyl-10-hydroxy-camptothecin (SN-38); and (b) a mixture of pharmaceutically acceptable excipients comprising (i) N-Methylpyrrolidone; and (ii) Vitamin E TPGS or a copolymer, the copolymer being 50/50 poly(lactic-co-glycolic acid), or 75/25 poly(lactic-co-glycolic acid) (PLGA); with the provision that if the VitE TPGS is present, the mixture of the excipients further comprises a polymer selected from the group consisting of Hydroxypropyl cellulose, Hydroxypropyl methylcellulose, VP/VAc copolymer 60/40, poloxamer 407, and Lauroyl Macrogol-32 glycerides; wherein the pharmaceutical composition contains no water; is in a liquid or a gel form, and the SN-38 is dissolved in the mixture of the excipients without precipitation.

8 Claims, 4 Drawing Sheets

FORMULATIONS WITH ENHANCED SN-38 SOLUBILITY AND ORAL ABSORPTION

REFERENCE TO RELATED APPLICATION

The present application claims the priority to U.S. Provisional Application Ser. No. 63/240,990, filed Sep. 5, 2021, which is herein incorporated by reference in its entireties.

FIELD OF THE INVENTION

The present invention relates generally to SN-38, and more specifically to formulations with enhanced SN-38 solubility and oral absorption.

BACKGROUND OF THE INVENTION

SN-38 or 7-Ethyl-10-hydroxy-camptothecin is an antineoplastic drug. It is the active metabolite of CPT-11 (irinotecan). CPT-11 is aqueous soluble. It is given intravenously. CPT-11 (HCl salt) aqueous solubility is said to be 25 mM in water (~15 to 16 mg/mL). In contrast, SN-38 is very poorly soluble (S<10 µg/mL). Bioconversion of irinotecan to SN-38 is basically species-dependent. In humans, the bioconversion to form SN-38 is slow and limited (~5%); about 33-66% of irinotecan remained unhydrolyzed at the end of a 24-hour infusion. (Rowinsky et al., CANCER RESEARCH 54, 427-436, Jan. 15, 1994).

SN-38 has been found to be 200-2000 times more cytotoxic than CPT-11, but it has not been used as an anticancer drug due to its poor solubility in pharmaceutically acceptable solvents and low affinity to lipid membranes. SN-38 has shown its in vitro and in vivo anti-tumor effects against various tumor cell lines and animal models of human cancer, such as ovarian (Zhang et al., J. Controlled Release 166 (2013) 147-158), breast (Sapra et al., Clin Cancer Res 2008; 14(6): 1888-1895), colorectal (Ibid), gastric (Tanaka et al., ONCOLOGY REPORTS 14:683-688, 2005), and pancreatic (Basel et al., *Small.* 2012; 8(6):913-920) cancer xenografts. SN-38 is basically insoluble in water (<40 µg/mL) and all the other pharmaceutically approved solvents (Zhang et al., Intl J. Pharmacol. 270 (2004) 93-107). Although SN-38 is known for its excellent anti-tumor ability, the extremely poor solubility of SN-38 hampers its development heavily by administration via either intravenous or oral route.

SUMMARY OF THE INVENTION

In one aspect, the invention relates to a pharmaceutical composition comprising: a) 7-Ethyl-10-hydroxy-camptothecin (SN-38); and b) a mixture of pharmaceutically acceptable excipients, comprising: (i) N-Methylpyrrolidone (NMP); and (ii) Vitamin E TPGS (VitE TPGS) or a copolymer, the copolymer being 50/50 poly(lactic-co-glycolic acid), or 75/25 poly(lactic-co-glycolic acid) (PLGA); with the provision that if the VitE TPGS is present, the mixture of the excipients further comprises a polymer selected from the group consisting of Hydroxypropyl cellulose (HPC), Hydroxypropyl methylcellulose (HPMC), VP/VAc copolymer 60/40, poloxamer 407, and Lauroyl Macrogol-32 glycerides; wherein the pharmaceutical composition contains no water, is in a liquid or a gel form, and the SN-38 is dissolved in the mixture of the excipients without precipitation.

In one embodiment, the mixture of the excipients in the pharmaceutical composition of the invention comprises: (i) NMP; (ii) VitE TPGS; and (iii) the polymer selected from the group consisting of HPC, HPMC, VP/VAc copolymer 60/40, poloxamer 407, and Lauroyl Macrogol-32 glycerides.

In another embodiment, the mixture of the excipients is chosen from: (i) a weight ratio of NMP, VitE TPGS, and HPC from 50:20:1 to 50:20:2.0; (ii) a weight ratio of NMP, VitE TPGS, and HPMC from 50:20:1 to 50:20:2.0; (iii) a weight ratio of NMP, VitE TPGS, and VP/VAc copolymer 60/40 of 50:20:20.0; (iv) a weight ratio of NMP, VitE TPGS, and poloxamer 407 of 50:20:20.0; or (v) a weight ratio of NMP, VitE TPGS, and Lauroyl Macrogol-32 glycerides of 50:20:20.0.

In another embodiment, the weight ratio of NMP, VitE TPGS, and HPC is from 50:20:1.0 to 50:20:2.5. In another embodiment, the weight ratio of NMP, VitE TPGS, and the polymer is from 50:20:2.5 to 50:20:5.0. The weight ratio of NMP, VitE TPGS, and HPC may be from 50:20:2.0 to 50:20:5.0.

In another aspect, the invention relates to a pharmaceutical composition comprising: a) 7-Ethyl-10-hydroxy-camptothecin (SN-38); and b) a mixture of pharmaceutically acceptable excipients, comprising: (i) N-Methylpyrrolidone (NMP); and (ii) Vitamin E TPGS (VitE TPGS), or a copolymer selected from 50/50 poly(lactic-co-glycolic acid) or 75/25 poly(lactic-co-glycolic acid) (PLGA); wherein the pharmaceutical composition contains no water, is in a liquid or a gel form, and the SN-38 is dissolved in the mixture of the excipients without precipitation.

In one embodiment, the mixture of the excipients comprises: (i) NMP; (ii) VitE TPGS; and (iii) a polymer selected from the group consisting of HPC, HPMC, VP/VAc copolymer 60/40, poloxamer 407, Lauroyl Macrogol-32 glycerides, and a copolymer of 50/50 PLGA or 75/25 PLGA.

In another embodiment, the mixture of the excipients comprises the NMP, and the copolymer selected from 50/50 PLGA or 75/25 PLGA; and further wherein the pharmaceutical composition is a gel form.

In another embodiment, 50/50 PLGA versus NMP is at a weight ratio of 1:3, and 75/25 PLGA versus NMP is at a weight ratio of 1:2.

In another embodiment, the polymer is selected from HPC or VP/VAc copolymer 60/40.

In another embodiment, the pharmaceutical composition is in an oral dosage form. In another embodiment, the polymer is HPC, and the pharmaceutical composition is in an oral dosage form. In another embodiment, the composition is in capsule form or liquid-in-syringe form. The composition may be formulated as capsule form, a liquid oral dosage form, or liquid-in-syringe form.

In another embodiment, the pharmaceutical composition may be a gel form or a thickened liquid.

In another embodiment, the mixture of the excipients forms a solution.

In another embodiment, the solubility of SN-38 is higher than 9 mg/g but lower than 19 mg/g at 20° C. except for the mixture of the excipients containing poloxamer 407 at 20° C.

In another embodiment, the polymer is selected from HPC or HPMC, and the solubility of SN-38 is higher than 9 mg/g but lower than 15 mg/g at 20° C.

In another embodiment, the mixture of the excipients comprises the copolymer and the solubility of SN-38 is no lower than 10 mg/g at 20° C.

Further in another aspect, the invention relates to use of a pharmaceutical composition in the manufacture of a medicament for treating cancer in a subject in need thereof.

The invention also relates to a method of treating cancer, comprising administering a therapeutically effective amount of a pharmaceutical composition according to the invention to the subject in need thereof to treat the cancer.

In one embodiment, the cancer is at least one selected from the group consisting of liver, pancreatic, colon, ovarian, breast, gastric and colorectal cancer.

DETAILED DESCRIPTION OF THE INVENTION

Definitions

Figure 1:
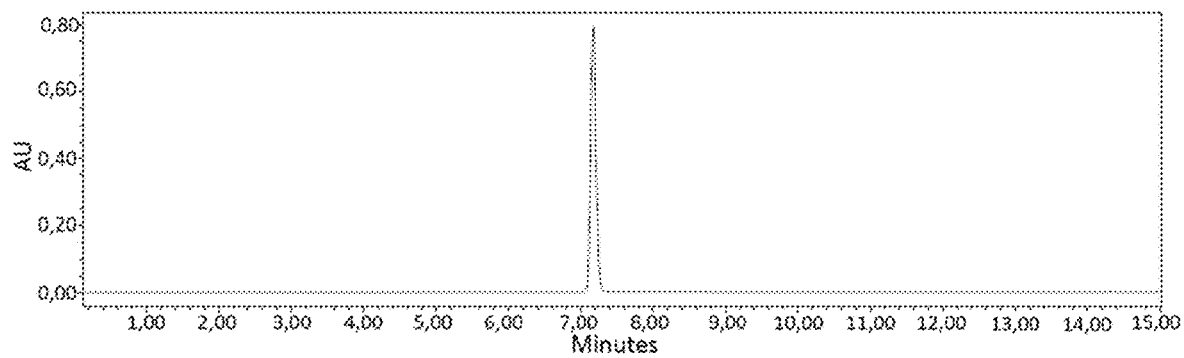
FIG. 1 is an HPLC chromatogram of a SN-38 standard solution.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only.

Unless otherwise defined, all technical and scientific terms used herein have the same meaning as commonly understood by one of ordinary skill in the art to which this invention pertains. In the case of conflict, the present document, including definitions will control.

The term "solution" is defined as a homogeneous mixture of one or more substances (solutes) dispersed molecularly in a sufficient quantity of dissolving medium (solvent).

As used herein, the terms "a formulation", "a composition", "a pharmaceutical mixture", "a pharmaceutical composition", are interchangeable.

As used herein, "formulation" refers to "any mixture or substance prepared according to a particular formula"; and/ or "a medicinal preparation formulated in a specific form, such as but not limited to a capsule.

The term "composition" refers to the resulting state or product; and/or an aggregate material formed from two or more substances.

As used herein, "preparation" refers to the state of being prepared; and/or "something prepared, manufactured.

As used herein, the term "except" is defined as "with the exclusion of", "excluding".

A gel or gel-liquid form is a colloid in a more solid form than a solution. Sometimes, they are also called "semi-solid" or "non-aqueous liquid" form, depending mostly upon their viscosity.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

The term "treating", or "treatment" refers to administration of an effective amount of a therapeutic agent to a subject, who has a disease, or a symptom or predisposition toward such a disease, with the purpose to alleviate, relieve, remedy, or ameliorate the disease, the symptoms of it, or the predispositions towards it.

The term "$C_{24}$" refer to the measured drug concentration recorded at 24 hrs post-dose.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

The range of body weight of the animals used in in-vivo experiments is from 19.4 to 24.7 g. Averaged weight was about 22.5 g.

Synonyms:

GELUCIRE® 50/13: stearoyl polyoxyl-32 glycerides; stearoyl polyoxyl/macrogol 32 glycerides.

GELUCIRE® 48/16: polyethylene glycol monostearate; PEG-32 stearate.

GELUCIRE® 44/14: Lauroyl polyoxyl-32 glycerides; Lauroyl polyoxyl/macrogol 32 glycerides; Lauroyl Macrogol-32 glycerides; Lauroyl PEG-32 glycerides.

KOLLIDON® VA 64: VP/Vac copolymer 60/40, which is 60% VP (vinylpyrrolidone)/40% VA (vinyl acetate), also named copovidone, Copolyvidone, vinylpyrrolidone-vinyl acetate copolymer, copolymer of 1-vinyl-2-pyrrolidone and vinyl acetate in a ratio of 6:4 by mass.

TPGS, Vitamin, E polyethylene glycol succinate, Vitamin E-TPGS, D-α-Tocopherol polyethylene glycol succinate, D-α-Tocopheryl polyethylene glycol 1000 succinate are synonyms.

LUTROL® F 127 is poloxamer 407, which is poly (ethylene glycol)-block-poly (propylene glycol)-block-poly (ethylene glycol).

Abbreviations

NMP: N-Methylpyrrolidone; VitE TPGS: D-α-Tocopheryl polyethylene glycol 1000 succinate; VP/Vac copolymer 60/40: 1-vinyl-2-pyrrolidone-vinyl acetate copolymer 60/40;

HPC: Hydroxypropyl cellulose; HPMC: hydroxypropyl methylcellulose; PO: Orally; PEG: Polyethylene glycol; QD: Once daily; SEM: Standard error of the mean.

Utility:

The invention relates to an innovative oral formulation of SN-38, the active metabolite of irinotecan. Oral anti-tumor or anti-cancer formulations or pharmaceutical compositions are disclosed for use in treating colorectal, liver, and pancreatic cancer, etc. The pharmaceutical compositions have reduced systemic side effects as compared with commercial injection product irinotecan. Additional advantages of the pharmaceutical compositions according to the invention include convenient use and better patient compliance (oral versus intravenous injection). The composition or formulation of the invention exclude any liposomal formulation and any solid form. In other words, the composition of the invention does not include any liposome or any solid form. It may be either semisolid or liquid formulations. As used herein, the composition of the invention is in semisolid or liquid form.

Both irinotecan and SN-38 are the derivatives of camptothecin. They are not New Chemical Entity (NCE). Irinotecan, synthesized from SN-38 by adding a water-soluble moiety, is regarded as the prodrug of SN-38 because the aqueous solubility of SN-38 is extremely low. SN-38 interferes with topoisomerase enzymes (topoisomerase I) which control the manipulation of the structure of DNA necessary for replication.

Irinotecan has already been marketed as CAMPTOSAR® (Pfizer) via intravenous infusion and used as a potent anti-cancer drug product, while currently no pharmaceutical product of SN-38, either administered orally or intravenously, has been approved or commercially available worldwide. An oral formulation of SN-38 should reduce the drug burden of using irinotecan by at least 20-fold, yet it should not compromise the overall therapeutic benefit in treating cancer patients. As compared to intravenous administered irinotecan, the Applicant has demonstrated equal, if not greater absorption, across several organ tissues to include liver, pancreas, and colon. The composition product of the invention provides sufficient SN-38 to the targeted tumor tissues and low systemic plasma levels.

Figure 6A:
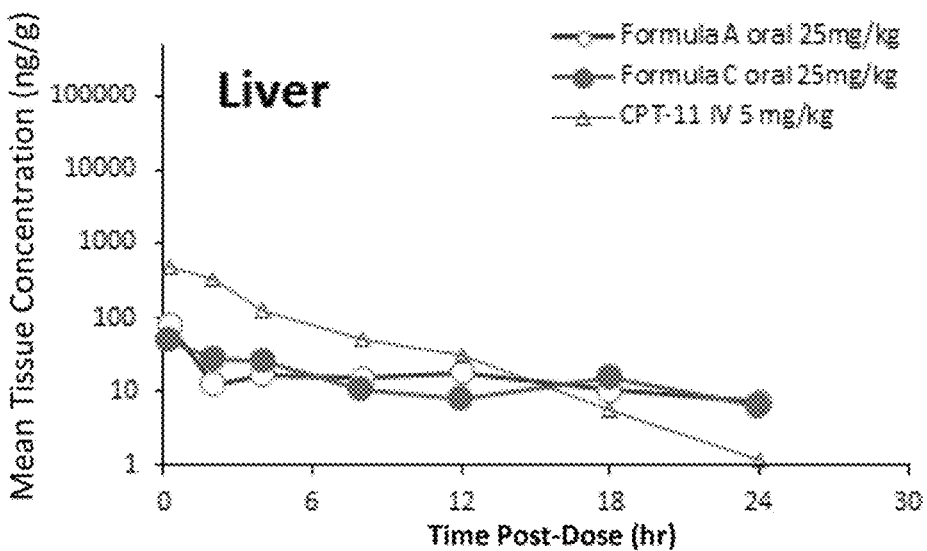
FIGS. 6A-C are charts showing tissue concentration versus time profile.

Irinotecan has already been approved for colorectal and pancreatic cancer. The Applicant here shows that preclinical data suggests that oral formulations of SN-38 ("TRX-920") could also have potential in treating liver cancer and pancreatic cancer. Pharmacokinetic studies show that long half-life results in a sustained-release profile of SN-38 in plasma and targeted tissues (FIG. 6A). Oral administration should result in better patient compliance due to increased convenience. Oral Formula A or C showed sustained SN-38 concentrations in liver tissue, meaning much longer half-life of SN-38 oral formulation than CPT-II given intravenously (FIG. 6A). Oral Formula A or C showed much higher SN-38 concentrations and drug exposure $AUC_{0-24}$ than CPT-11 (iv) in colon tissue by at least 20-fold. Overall, we believe the drug distribution data would support the use of oral SN-38 formulation in treating colon cancer more effective therapeutically than conventional intravenous injection of CPT-11 (FIG. 6C). Other potential benefits provided by oral formulations of SN-38 according to the invention include:

(1) Allow cancer patients with irinotecan-associated "hereditary fructose intolerance" to benefit from oral SN-38.

(2) Reduce antigenicity, emesis, or myelosuppression when compared to intravenous irinotecan. This was evident by the reduced antigenicity as SN-38 demonstrated no antigenic potential in guinea pig, whereas irinotecan has shown antigenic potential in guinea pig and rabbit; and (3) Reduce emetic effects with SN-38 treatment in animal studies. At 20 mg/kg (i.v.) of irinotecan, five of six dogs showed emesis within 1 to 2 minutes of drug administration. At 40 mg/kg of irinotecan, emesis was induced in 1 minute, and the two dogs died 3 and 6 minutes later. When SN-38 (11.6 mg/kg, i.v.) was administered to the dogs, no emesis or nausea was noted (PRODUCT MONOGRAPH, Pr Irinotecan Hydrochloride Injection, by Auro Pharma Inc. Ontario, CANADA, Submission Control Number: 216121, June 2020, page 44.)

Examples (A) Formulation Design and Development

I. Screening of Excipients

We screened various types of oral excipients and excipient combinations for their ability to enhance SN-38 solubility, with the objective of identifying orally acceptable semi-solid or liquid formulations such as viscous emulsion or gel that could be filled into either soft or hard-shell capsules or pre-filled syringe for oral use. Various combinations of SN-38 with different solvents and excipients were tested. These preliminary prototype formulations would be used in animal experiments for assessing SN-38 oral bioavailability and GI-tract local tolerance after oral dosing.

The first step of this study is formulation screening to identify vehicle(s) that solubilize(s) the best for the SN-38 compound. A concentration of 50 mg/mL is targeted. In a second step, excipient mixtures are tested with a new (lower) target of 20 mg/mL.

II. Materials and Methods

II.1 Compound.

Table 1 presents tested compound.

TABLE 1

| Compound name | Compound batch | compound code | sample code |
|---|---|---|---|
| SN-38 | JH1312 | DA144002 | EX2503 |

II.2 Reactants and Excipients

Table 2 presents the list of the references of the best excipients used for the study and reactants.

TABLE 2

| Reactants/Excipients | Other name | Reference and batch |
|---|---|---|
| Cremophor EL | Cremophor | BASF ref. 51635553 - batch 73483816KO |
| Propylene glycol | PG | SIGMA ALDRICH ® ref. 16033-1L - batch SZBC0820V |
| Capmul MCM | Capmul | Abitec corporation - batch 120105-6 |
| Labrafil 1944CS | / | Gattefosse ref. 3063BAZ - batch 154428 |
| N-Methylpyrrolidone | NMP | VWR Chemicals Ref. 26211.298 -batch 13F280503 |

TABLE 2-continued

| Reactants/Excipients | Other name | Reference and batch |
|---|---|---|
| Polysorbate 20 | Tween 20 | Fluka ref. 44112 batch BCBJ3350V |
| Vitamin E TPGS | VitE TPGS | Isochem batch 1301040011 |
| Isopropyl myristate | IPM | Fluka ref. 70120 batch 1216171 |
| Miglyol 812N | \ | Sasol batch 100804 |
| Labrafac lipophile WL1349 | \ | Gattefosse ref. 3139JV1 batch 156244 |
| Lauroglycol 90 | \ | Gattefosse ref. 3244BAZ batch 140723 |
| Noveon AA1 Polycarbophil | \ | Lubrizol ref. NOV1001 batch 0101331066 |
| Carbopol 971P | \ | Lubrizol ref. CBP1052 batch 0101249012 |
| Carbopol 974P | \ | Lubrizol batch 0100655877 |
| Hydroxypropyl methylcellulose Methocel E4M | HPMC E4M | Colorcon ref. ID34516 batch DT372097 |
| Hydroxypropyl methylcellulose Methocel E10M | HPMC E10M | Colorcon ref. ID3172 batch DT349011 |
| Methylcellulose Methocel A15C | MC A15C | Colorcon ref. ID3178 batch DT353985 |
| Hydroxypropyl cellulose Klucel MF Pharm | HPC | Ashland ref. 414377 lot 53470 |
| GELUCIRE ® 44/14 (Lauroyl Macrogol-32 glycerides) | GELUCIRE ® | Gattefosse ref. 3051PP1 batch 136981 |
| KOLLIDON ® VA64 | \ | BASF ref. 50347977 batch 39936956P0 |
| LUTROL ® F127 | \ | BASF ref. 51632903 batch WPMF542B |
| PVP K90 | \ | BASF ref. 50000784 batch 25749156P0 |
| Acetonitrile | CH3CN | SIGMA ALDRICH ® ref. 34851 batch STBF0788V |
| 50/50 Poly (D, L-lactide-co-glycolide), acid-terminated, IV 0.4 dl/g, Mw 35000 | 50/50 PLGA | Polysciences Europe GmbH ref. 26270-10 lot 691544 |
| 75/25 Poly (D, L-lactide-co-glycolide), acid terminated, IV 0.2 dl/g, Mw 15000 | 75/25 PLGA | Polysciences Europe GmbH ref. 26268-10 lot 691542 |
| Dimethylsulfoxide | DMSO | SIGMA ALDRICH ® ref. 34869 batch STBF3447V |
| Ethanol | EtOH | Carlo Erba ref. 412522 batch P013A3721 |
| De-ionized water | H2O | / |

II.3 Formulation Screening

The saturation is obtained by adding gradually an excess of active ingredient (maximum target being 50 mg/mL) to a given volume of test medium. When the samples seem to be saturated, they are stirred by magnetic stirring over 24 hours at 20° C., protected from light.

The supernatant is then isolated, diluted in a solvent mixture allowing its injection into the chromatographic system. The concentration in solution for each medium is determined by HPLC (external standardization).

II.4 HPLC.

Table 3 presents HPLC method.

TABLE 3

| HPLC system | Injector/Pump: Alliance 2695 Waters |
| | Detector: Photo Diode Array 996 Waters |
| | Software: Millennium32 (version 3.20 or 4.0) Water |
| Column | Waters Symmetry shield RP18 |
| | 150 mm × 4.6 mm (d), size = 5 µm |
| Mobile phase | A: H$_2$O/TFA 0.05% |
| | B: CH$_3$CN/TFA 0.05% |

| Time (min) | A % | B % |
|---|---|---|
| 0 | 95 | 5 |
| 1 | 95 | 5 |
| 9 | 10 | 90 |
| 12 | 10 | 90 |
| 12.1 | 95 | 5 |
| 15 | 95 | 5 |

| Flow rate | 1 mL/min |
| Column Detection | Temperature Room temperature |
| | UV: 1 = 365 nm |
| Standard solution | From 1 µg/mL to 100 µg/mL in H$_2$O/CH$_3$CN 20/80 (v/v) |

TABLE 3-continued

| Test solution | Suitable dilution with H$_2$O/CH$_3$CN 20/80 (v/v) or appropriate solvent |
| Injection volume | 10 µL |
| Injector temperature | 20° C. |
| Retention time | ≈7.2 min |

III Results

III.1 Oral Solution Screen

III.1.1 Formulation Screening.

A concentration of 5 mg/mL is first targeted, bulk having to be added if the 5 mg/mL are soluble. None of the tested media reaches 5 mg/mL, except the NMP sample which requires 50 mg of bulk per mL to be saturated. After 24 h of magnetic stirring, all samples are confirmed to be saturated and are analyzed. The resulting solubility levels (HPLC results) are presented in the table below for the 6 best excipients or solutions of excipients (from a list of 10 tested excipients). Table 4 presents Formulation screening results.

TABLE 4

| Media | SN-38 solubility (mg/g) |
|---|---|
| NMP | 42 |
| Propylene glycol | 1.15 |
| Capmul MCM | 0.32 |
| Labrafil M1944CS | 0.054 |
| Cremophor EL at 30% in water | 0.017 |
| VitE TPGS at 20% in water | ≈0.01 |

As expected, SN-38 appears to be very poorly soluble in most tested media and the solubility results are far from the 50 mg/mL target, except for NMP, in which SN-38 solubility reaches 42 mg/g. In propylene glycol and Capmul MCM, SN-38 is respectively soluble at 1.15 mg/g and 0.054 mg/g. In all other tested media, SN-38 solubility is lower than 0.054 mg/g.

III.1.2 Tentative Formulation Optimization.

To try to increase concentration of SN-38 in formulation that could be tested in animals, combination of best excipients is now considered. Based on the fact NMP is the best solubilizer for SN-38 and given the fact 20 mg/mL is the new target, the following mixtures are then selected:
  (i) NMP/VitE TPGS/Capmul MCM/Tween 20 (50/20/10/20—w/w)
  (ii) NMP/VitE TPGS/IPM/Solutol HS15 (50/20/10/20—w/w)
  (iii) NMP/VitE TPGS/Mygliol 812/Propylene glycol (50/20/10/20—w/w)
  (iv) NMP/VitE TPGS/Labrafac Lipophile WL1349/Lauroglycol (50/20/10/20—w/w)

Table 5 presents SN-38 solubility (HPLC results) in different mixtures.

TABLE 5

| Mixtures (% w) | SN-38 solubility (mg/g) |
| --- | --- |
| NMP (50) VitE TPGS (20) Capmul MCM (10) Tween 20 (20 | 7.57 |
| NMP (50) VitE TPGS (20) Isopropyl myristate (10) Solutol HS15 (20) | 9.04 |
| NMP (50) VitE TPGS (20) Mygliol 812 (10) Propylene glycol (20) | 5.95 |
| NMP (50) VitE TPGS (20) Labrafac Lipophile WL1349 (10) Lauroglycol 90 (20) | 2.76 |

Despite the remaining amount of NMP (50% in each of these 4 new media), none of these mixtures allows solubilizing SN-38 at 20 mg/g.

In the mixture "NMP/Vit E TPGS/IPM/Solutol HS15 (50/20/10/20—w/w)", SN-38 solubility reaches 9.04 mg/g.

Note 1: whatever the mixture, when the isolated saturated supernatant is extemporaneously diluted by a factor 2 by addition of water, a marked precipitation is immediately observed.

III.1.3 Interim Conclusion.

The target of 50 mg/mL soluble SN-38 has not been reached in any tested liquid excipients or in highly loaded aqueous solutions of surfactants. Solubility in NMP is quite high (42 mg/mL), but this excipient has only rarely been administered to patients (one identified injectable drug product) and would not be administered pure but likely in a mixture that remains to be defined.

Four excipient combinations have then been tested, comprising 50% of NMP (to try to stay around a target solubility of 20 mg/mL for SN-38) and introducing a medium length lipidic chain excipient plus surfactants. None of the tested mixtures has allowed reaching 10 mg/mL (9 mg/mL was obtained in a "NMP/Vit E TPGS/IPM/Solutol HS15 (50/20/10/20—w/w)" mixture.

Note: After dilution by a factor 2 in water, none of the 4 isolated saturated excipient mixtures has prevented the reprecipitation of SN-38.

III.2 Oral Bioavailability Enhancement Study

Further to previous results, additional experiments are performed by adding polymers in a vehicle containing NMP (solubilization of SN-38) and VitE TPGS (inhibition of P-glycoprotein and pre-hepatic cytochrome P450).

The polymer would possibly moderate the precipitation of SN-38 upon dilution in water. In a second step, additional SN-38 solubility measurement in polymer-containing NMP/VitE TPGS vehicles will be performed.

III.2.1 Polymer (3rd Excipient) Apparent Solubility in NMP.

Nine polymers and 1 GELUCIRE® are tested for their solubility in NMP with the objective of selecting "NMP+VitE TPGS+polymer" vehicle compositions.

The targeted 3rd excipient percentage versus NMP is 10% (w/w) and then 5% if not soluble at 10%. Table 6 presents polymer solubility in NMP.

TABLE 6

| Polymer | % Polymer versus NMP | Visual observation after one night at 20° C. | Estimated viscosity |
| --- | --- | --- | --- |
| PVP K90 | 10 | clear | like honey |
| KOLLIDON ® VA64 | 10 | clear | like water |
| LUTROL ® F127 | 10 | clear | like water |
| GELUCIRE ® | 10 | clear | like water |
| Noveon AA1 | 5 | turbid | non-flowing gel |
| Carbopol 971P | 5 | turbid | non-flowing gel |
| Carbopol 974P | 5 | turbid | non-flowing gel |
| HPMC Methocel E4M | 5 | clear | non-flowing gel |
| HPMC Methocel E10M | 5 | clear | non-flowing gel |
| MC Methocel A15C | 5 | slightly turbid | non-flowing gel |

Four tested polymers (PVP K90, KOLLIDON® VA64, LUTROL® F127 and GELUCIRE®) introduced at 10% in NMP lead to liquid mixtures. For KOLLIDON® VA64 and LUTROL® F127, given the low viscosity at 10% in NMP, it would be possible to increase to 20% in NMP for the next tests with an increased viscosity.

The other tested polymers (Carbopol 971P, Carbopol 974P, Noveon AA1, Methocel E4M, Methocel E10M, Methocel A15C) are either non-soluble or interestingly leading to gels (non-flowing gels/either clear or turbid).

III.2.2 Introduction of VitE TPGS in the Mixtures and SN-38 Solubility Measurement III.2.2.1 Solubility of Selected Excipients in Mixtures of NMP/VitE TPGS.

The 3 above selected polymers plus 1 GELUCIRE® are then introduced into an NMP/VitE TPGS mixture at the two following compositions: NMP/VitE TPGS/Polymer at 50/20/10 (w/w/w) or 50/20/20 (w/w/w). Table 7 presents polymer solubility in NMP/VitE TPGS mixture

TABLE 7

| Soluble Polymers | X (g) of polymer mixed to 5 g of NMP + 2 g of VitE TPGS | Visual observation of the mixture after one night at 20° C. [1] |
| --- | --- | --- |
| PVP K90 | 1 | not soluble and heterogeneous (liquid/gel) |
| KOLLIDON ® VA64 | 2 | clear |
| LUTROL ® F127 | 2 | clear |
| GELUCIRE ® | 2 | clear |

[1] or 25° C. for the mixture containing LUTROL ® F127 to avoid gelling

III.2.2.2 Solubility of SN-38 in NMP/VitE TPGS/Excipient Mixtures.

Solubility of SN-38 is then measured in the three other NMP/VitE TPGS/polymer mixtures as well as in the NMP/VitE TPGS mixture to make a comparison. Table 8 presents SN-39 solubility (HPLC results) in NMP/VitE TPGS/Polymer mixtures.

TABLE 8

| Mixtures (% w) | SN-38 Solubility [2] (mg/g) |
| --- | --- |
| NMP (50)<br>VitE TPGS (20) | 18.51 |
| NMP (50)<br>VitE TPGS (20)<br>KOLLIDON ® VA64 (20) | 15.65 |
| NMP (50)<br>VitE TPGS (20)<br>LUTROL ® F127 (20) | 10.02 |
| NMP (50)<br>VitE TPGS (20)<br>GELUCIRE ® (20) | 9.25 |

[2] at 20° C. except for the mixture containing LUTROL ® F127 (25° C.)

The maximum SN-38 solubility is reached in the mixture NMP/VitE TPGS 50/20 w/w where it even gets very close to the initial target concentration (20 mg/g). The addition of the tested excipients to this mixture does not improve the SN-38 solubility. Note: whatever the above tested new mixture, when a small volume of the isolated saturated supernatant is extemporaneously diluted by a factor 2 by addition of water, a marked precipitation is again immediately observed.

III.2.3 SN-38 Formulated in Gels

Several polymers lead to gel formation when solubilized in NMP. If feasible, a SN-38 formulation leading to a gel could be tested in animal pharmacokinetic studies to see if the modified release of SN-38 by this form could improve SN-38 oral absorption and bioavailability.

The first tested approach uses a solution of SN-38 in an NMP/VitE TPGS mixture (the mixture allowing the best solubility of the SN-38) to try to form gels by addition of various polymers of interest, checking at the same time if SN-39 stays soluble in each final mixture. Before engaging SN-38, for each tested polymer, its solubility is first verified in the NMP/VitE TPGS 50/20 w/w as well as its ability to form a gel. Table 9 presents Gelling/thickening polymer visual solubility check in an NMP/VitE TPGS mixture.

Based on the apparent viscosity of the tested mixtures, as well as on the presence of a remaining a non-solubilized polymer fraction, the selected percentage of HPMC E4M and HPMC E10M will be 4% (% w versus NMP) for further tests with SN-38.

For HPC, both above tested percentages (2 and 5%) will be further tested with SN-38. Given the previously measured SN-38 solubility at saturation in the NM/VitE TPGS 50/20 mixture (≈18.5 mg/g), a solution at 15 mg/g of SN-38 will be tested. This starting solution is prepared by over stirred 24 hours at 20° C. and then filtered before being used for into polymer solubilization.

The three polymers of interest (HPMC E4M, HPMC E10M, and HPC Klucel) are weighed (according to the above selected percentages) and added for solubilization and under stirring onto the SN-38 solution in NMP/VitE TPGS 50/20 mixture. After 24 h stirring at 20° C., the 3 samples are visually observed, and their SN-38 content is assessed by HPLC (after dilution in an appropriate solvent).

SN-38 Formulated Samples in NMP/VitE TPGS/HPC (50 w:20 w:5% w Versus NMP).

Excipients: N-methyl-pyrrolidone (NMP); Vitamin E TPGS (VitE TPGS); Hydroxypropyl cellulose (HPC).

Media Composition for Solubilizing Sn-38

Media: NMP/VitE TPGS 50 w:20 w

Composition: For preparing 70 g of vehicle: (1) Allow the VitE TPGS (solid at room temperature) to melt at 60° C., (2) Introduce 50 g of NMP and 20 g of VitE TPGS into an appropriate bottle, (3) Mix the vehicle components until the mixture looks homogeneous, by means of an efficient magnetic stirring.

Protocol for Preparing the SN-38 Formulated Samples at 3.75 mg/g in NMP/VitE TPGS/HPC Manufacturing of the Solubilizing Medium of SN-38:

The "NMP/VitE TPGS 50 w:20 w" vehicle is first prepared by simple mixing (as described above).

Preparation of SN-38 solution: The required quantity of SN-38 is accurately weighed in a glass vessel of appropriate volume. The desired volume of the previously prepared vehicle (NMP/VitE TPGS 50 w:20 w) is then added onto the SN-38 API powder to obtain a concentration of 3.89 mg/g* (*: concentration that considers the final small dilution after the final addition of the 5% HPC (5% w versus NMP)). The preparation is then stirred, protected from light, overnight or until complete solubilization is observed. Note: The SN-38 solution is yellow-colored, as the final "gel" is.

TABLE 9

| Tested polymers | % Of polymer vs the NMP present in the NMP/VitE (50/20) mixture | Visual observation after one night of stirring at 20° C. | Estimated viscosity |
| --- | --- | --- | --- |
| Noveon AA1 | 3 | not soluble | N/A |
| Carbopol 971P | 3 | not soluble | N/A |
| Carbopol 974P | 5 | not soluble | N/A |
| HPMC Methocel E4M | 2 | soluble | like honey |
| HPMC Methocel E4M | 5 | not fully soluble | flowing gel |
| HPMC Methocel E10M | 2 | soluble | like honey |
| HPMC Methocel E10M | 5 | not fully soluble | non-flowing gel |
| MC Methocel A15C | 3 | turbid | like water |
| HPC Klucel | 2 | soluble | flowing gel |
| HPC Klucel | 5 | very slightly turbid | non-flowing gel |

Four of the tested polymers (Noveon AA1, Carbopol 971P, Carbopol 974P and Methylcellulose A15C) are not soluble in the NMP/VitE TPGS (50/20) mixture. The three other tested polymers lead to gels (or thickened liquids).

Thickening of the SN-38 Solution

The required quantity of HPC (corresponding to 5% w/w versus the mass of NMP present in the sample) is accurately weighed in an appropriate flask. The HPC is then sprinkled (fast but without forming agglomerates) onto the previously prepared SN-38 solution in NMP/VitE TPGS (while that solution is maintained under vigorous magnetic stirring). Magnetic stirring is maintained for a few minutes, until (thickening being almost complete) the viscosity of the formulation prevents the magnetic bar to continue to stir. The glass flask is then transferred onto an orbital shaker for stirring for one more day (or at least one night) to complete the solubilization of the HPC and the homogenization of the final sample. After the thickening of the SN-38 is completed, the formulation is ready to use and can be aliquoted. *Note: the whole process is conducted at room temperature (about 20-25° C.). Table 10 presents results of macroscopic observations of SN-38 "gels". Table 11 presents HPLC results of SN-38 gels.

TABLE 10

| Percentage of polymer [1] | Visual observation | Visually estimated viscosity |
|---|---|---|
| No polymer in NMP/VitE TPGS (50 w/20 w) | Homogeneous yellow solution | Like water |
| 5% HPC (vs NMP) in NMP/VitE TPGS (50 w/20 w) | Homogeneous yellow gel | Non-flowing solution |
| 2% HPC (vs NMP) in NMP/VitE TPGS (50 w/20 w) | Homogeneous yellow gel | like honey |
| 4% HPMC E4M (vs NMP) in NMP/VitE TPGS (50 w/20 w) | Homogeneous yellow gel | slightly flowing solution |
| 4% HPMC E10M (vs NMP) in NMP/VitE TPGS (50 w/20 w) | Homogeneous yellow gel | slightly flowing solution |

[1] The indicated percentage of polymer is calculated versus the amount of NMP content present in the NMP/VitE mixture.

TABLE 11

| Formulation [1] | Theoretical SN-38 content (mg/g) in the formulation | SN-38 content (mg/g) calculated by HPLC |
|---|---|---|
| No polymer in NMP/VitE TPGS (50 w/20 w) | \ | 14.47 |
| 5% HPC (vs NMP) in NMP/VitE TPGS (50 w/20 w) | 13.98 | 13.95 |
| 2% HPC (vs NMP) in NMP/VitE TPGS (50 w/20 w) | 14.26 | 14.32 |
| 4% HPMC E4M (vs NMP) in NMP/VitE TPGS (50 w/20 w) | 14.07 | 14.03 |
| 4% HPMC E10M (vs NMP) in NMP/VitE TPGS (50 w/20 w) | 14.07 | 14.00 |

[1] The indicated percentage of polymer is calculated versus the amount of NMP content present in the NMP/VitE (5 w/2 w) mixture.

No SN-38 precipitation is observed when the polymers are added onto the SN-38/NMP/VitE TPGS solution for gelling. The different resulting final SN-38 formulations are homogeneous "gels" (more or less viscous clear yellow solutions). Note: adding 1 volume of water onto 1 volume of each of these (SN-38 saturated) gels leads to significant SN-38 precipitation.

III.2.4 SN-38 Formulated with PLGA

Before engaging the selected PLGA in tentative SN-38 formulations, the solubility of both polymers is first visually verified in NMP at a starting mass ratio of 1:2 (w:w) (i.e., 1 g of PLGA for 2 g of NMP). The 50/50 PLGA polymer being not fully soluble in these conditions, it is tested again at a 1:3 mass ratio (see Table 12). Table 12 presents PLGA visual solubility check in NMP.

TABLE 12

| Tested PLGA | Ratio vs NMP | Visual observation after one night of stirring at 20° C. | Estimated viscosity |
|---|---|---|---|
| 50/50 PLGA | 1:2 | not fully soluble | N/A |
| 50/50 PLGA | 1:3 | soluble | like honey |
| 75/25 PLGA | 1:2 | soluble | like honey |

Note:
a slight heating (at about 40° C.) helps PLGA dissolution.

SN-38 solubilization in these two PLGA/NMP solution mixtures is then tested with a SN-38 starting concentration of 20 mg/g and then decreasing the tested concentration if needed. Table 13 presents the results of macroscopic observation of tentative SN-38 solubilization in PLGA/NMP mixtures

TABLE 13

| Tested PLGA/NMP mixture | SN-38 concentration (mg/g) | Visual observation |
|---|---|---|
| PLGA (50:50): NMP mass ratio of 1:3 (1 g of 50/50 PLGA for 3 g of NMP) | 20 | not fully soluble |
|  | 15 | soluble |
| PLGA (75:25): NMP mass ratio of 1:2 (1 g of 75:25 PLGA for 2 g of NMP) | 20 | not soluble |
|  | 15 | not fully soluble |
|  | 10 | soluble |

Figure 2:
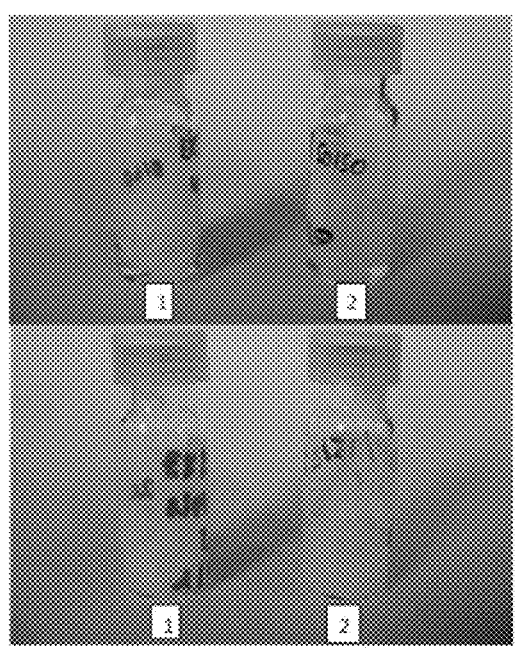
FIG. 2 show pictures of resulting samples after dilution in water. Top: PLGA (50:50):NMP at a mass ratio of 1:3; Bottom: PLGA (75:25):NMP at a mass ratio of 1:2. Sample #1: excipients (PLGA/NMP) mixture with SN-38; sample #2: excipients (PLGA/NMP) mixture alone (without SN-38).
Figure 3A:
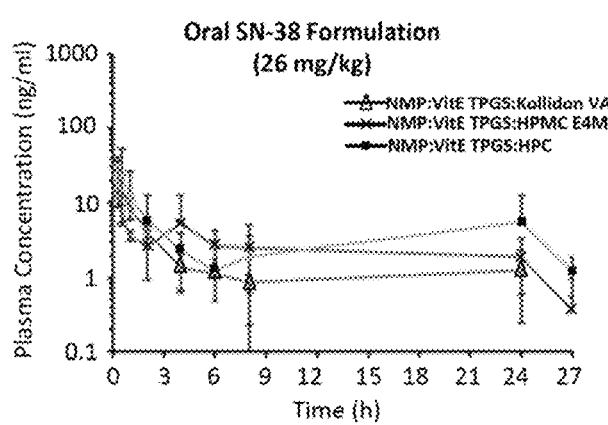
FIGS. 3A-B are charts showing plasma concentration versus time relationships.
Figure 3B:
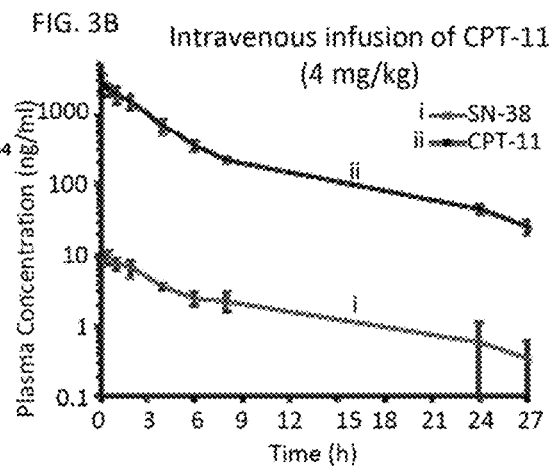

SN-38 is soluble at 10 mg/g in a PLGA (75:25):NMP mixture at the mass ratio of 1:2. A better SN-38 solubility is observed in the PLGA (50:50):NMP mixture at a mass ratio of 1:3, which is likely mostly due to the higher fraction of NMP in the test sample. Note: When these two SN-38 solutions (in NMP+PLGA) are extemporaneously diluted by a factor 2 by addition of water, a white precipitate is immediately observed (see FIG. 2). A very similar precipitation is also observed by diluting a placebo PLGA/NMP mixture (without SN-38) by water (it is not easy to visually differentiate the placebo and SN-38 containing formulation precipitate).

III.3 Conclusion

Among the different tested excipient combinations, a maximum SN-38 solubility has been reached in an NMP/VitE TPGS 50/20 (w/w) mixture (18.5 mg/g).

Addition of KOLLIDON® VA64 (2 w), LUTROL® F127 (2 w) or GELUCIRE® (2 w) to NMP/VitE TPGS (5 w/2 w) is possible and the mixture stays liquid, which allows measuring SN-38 solubility levels (respectively at 15.6 mg/g, 10.0 mg/g and 9.2 mg/g).

Addition of HPMC (E4M or E10M) or HPC Klucel allows forming "gels" by direct solubilization of each of these polymers by a 15 mg/g SN-38 solution in an NMP/VitE TPGS (5 w/2 w) mixture without precipitation of SN-38.

SN-38 is soluble at 10 mg/g in a PLGA (75:25):NMP mixture at the mass ratio of 1:2 and at 15 mg/mL in a PLGA (50:50):NMP mixture at the mass ratio of 1:3.

Addition of water to all samples leads to a significant precipitation.

(B) Animal Oral Pharmacokinetics and Tissue Distribution Studies

Rodent (rats) and non-rodent (Beagle dogs) studies to examine the pharmacokinetics (PK) of SN-38 and tissue distribution after oral administration in the selected formulations were conducted.

1. Pharmacokinetics of CPT-11/SN-38 Following a Single Intravenous Dose or a Single Oral Dose of CPT-11/SN-38 to Beagle Dogs.

(1) Study Design: Six male and three female non-naive Beagle dogs were treated with CPT-11 and SN-38 according to the regimen shown in Table 14.

TABLE 14

| Phase | Compound | Dose Route/ Formulation | Dose Level mg/kg | mL/kg | Analytes |
|---|---|---|---|---|---|
| 1 | SN-38 | Oral - Formula A NMP/VitE TPGS/ KOLLIDON ® VA64 (14.8 mg/mL) | 26 | 1.8 | SN-38 |
| 1 | SN-38 | Oral - Formula B NMP/VitE TPGS/ HPMC E4M (13.3 mg/mL) | 26 | 2 | SN-38 |
| 1 | SN-38 | Oral - Formula C NMP/VitE TPGS/ HPC (13.1 mg/mL) | 26 | 2 | SN-38 |
| 2* | SN-38 | Oral 35% PEG-400/ 5% Ethanol/Water | 3 | 1 | SN-38 |
| 2 | CPT-11 | IV Sorbitol/Lactic solution | 4 | 1 | CPT-11 & SN-38 |

*The dogs were not dosed due to the insolubility of compound in the formulation.

(2) Results. PK data:

TABLE 15

| PK Param- eters | Unit | SN-38 Oral A[a] SN-38 | SN-38 Oral B[b] SN-38 | SN-38 Oral C[c] SN-38 | CPT-11 IV 4 mg/kg SN-38 | CPT-11 IV 4 mg/kg CPT-11 |
|---|---|---|---|---|---|---|
| $T_{max}$ | h | 0.25 | 1.50 | 0.417 | 0.417 | NA |
| $C_{max}$ | ng/ml | 29.2 | 14.2 | 24.9 | 10.0 | NA |
| $AUC_{0-t}$ | ng h/ml | 48.3 | 68.7 | 114 | 55.6 | 10102 |
| $AUC_{0-\infty}$ | ng h/ml | 52.4 | 56.8 | 247 | 63.8 | 10344 |
| $t_{1/2}$ | h | 2.25 | 3.16 | 5.71 | 7.70 | 6.47 |

[a]Formula A: NMP:VitE TPGS:KOLLIDON ® VA64
[b]Formula B: NMP:VitE TPGS:HPMC E4M
[c]Formula C: NMP:VitE TPGS:HPC 2. Pharmacokinetics and Tissue Distribution of CTP-11/SN-38 Following a Single Intravenous Dose of CTP-11 or a Single Oral Dose of SN-38 Oral Formulations to Sprague-Dawley Rats.

Two (2) selected candidate formulations for further evaluation in animal pharmacokinetics studies: Formulation A (TRX-920A): Soluble at max. concentration of ~15 mg/g and Formulation C (TRX-920B): Soluble at max. concentration of ~15 mg/g.

Figure 4A:
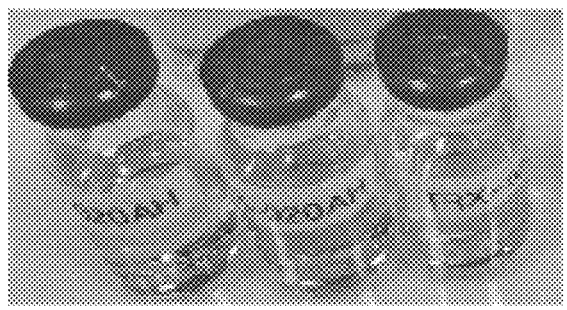
FIGS. 4A-B are photographs showing the appearances of Formula A and Formula C.
Figure 4B:
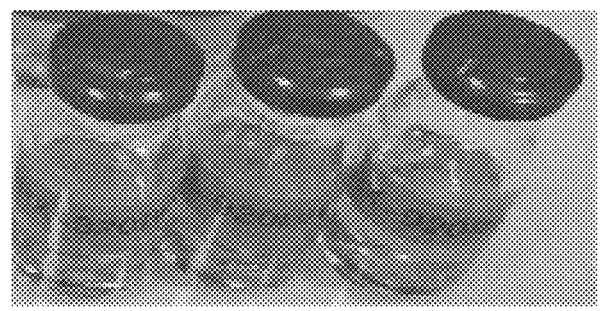

The appearance is different. Formula A (TRX-920AH) appeared to be a yellow viscous solution and Formula C (TRX-920BH) appeared to be a yellow gelled solution (FIGS. 4A-B).

(1) Study Design:

TABLE 16

| Phase | Compound | Dose Route/Vehicle | Dose Level mg/kg | mL/kg | Analytes |
|---|---|---|---|---|---|
| 1 | CPT-11 | IV Sorbitol/Lactic solution | 5 | 1.0 | CPT-11 & SN-38 |

TABLE 16-continued

| Phase | Compound | Dose Route/Vehicle | Dose Level mg/kg | mL/kg | Analytes |
|---|---|---|---|---|---|
| 2 | SN-38 | PO Formula A (14.8 mg/mL) | 25 | 2.1 | SN-38 |
| 3 | SN-38 | PO Formula C (13.1 mg/mL) | 25 | 2.4 | SN-38 |

TABLE 17

| PK Parameters | Unit | Formula A (Oral 25 mg/kg) SN-38 | Formula C (Oral 25 mg/kg) SN-38 | CPT-11 (IV 5 mg/kg) SN-38 | CPT-11 (IV 5 mg/kg) CPT-11 |
|---|---|---|---|---|---|
| $T_{max}$ | h | 0.417 | 2.06 | 0.222 | NA |
| $C_{max}$ | ng/ml | 0.496 | 0.432 | 438 | NA |
| $AUC_{0-t}$ | ng · h/ml | 4.94 | 3.89 | 676 | 129 |
| $AUC_{0-\infty}$ | ng · h/ml | NA | NA | 678 | 132 |
| $t_{1/2}$ | h | NA | NA | 4.19 | 0.271 |

Formula A: SN-38 in NMP:VitE TPGS:KOLLIDON® VA64 (50:20:20, w/w).

Formula C: SN-38 in NMP:VitE TPGS:HPC (50:20:5, w/w).

Figure 5A:
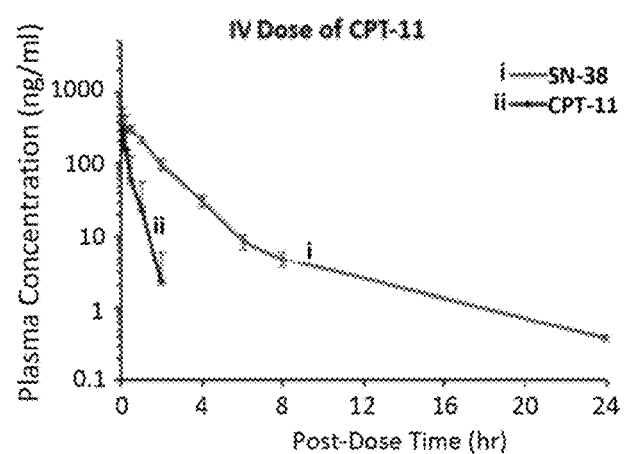
FIGS. 5A-B are charts showing plasma concentration versus time profile.
Figure 5B:
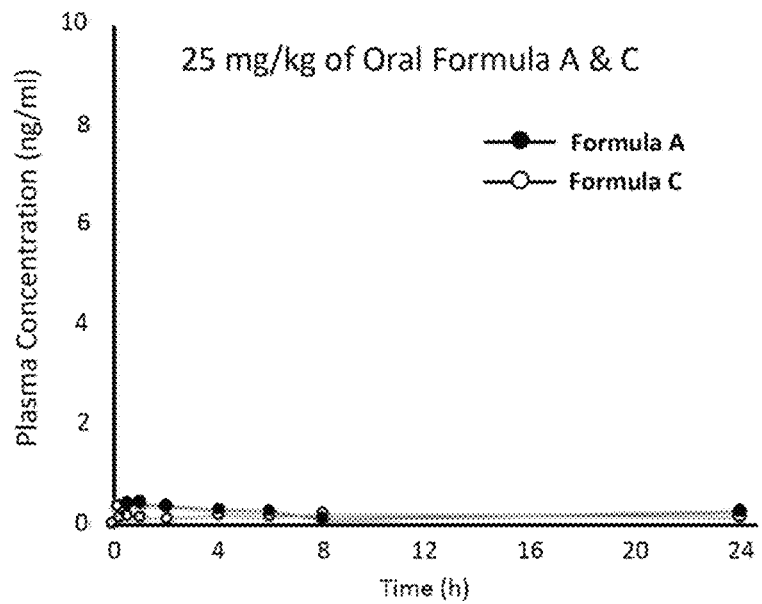

FIGS. 5A-B show plasma concentration versus time profiles of intravenous CPT-11 and oral Formulae of SN-38.

Low plasma SN-39 concentrations from Oral Formula A or C would expect to result in much less systemic side effects than IV injection of Irinotecan (CPT-11).

Figure 6B:
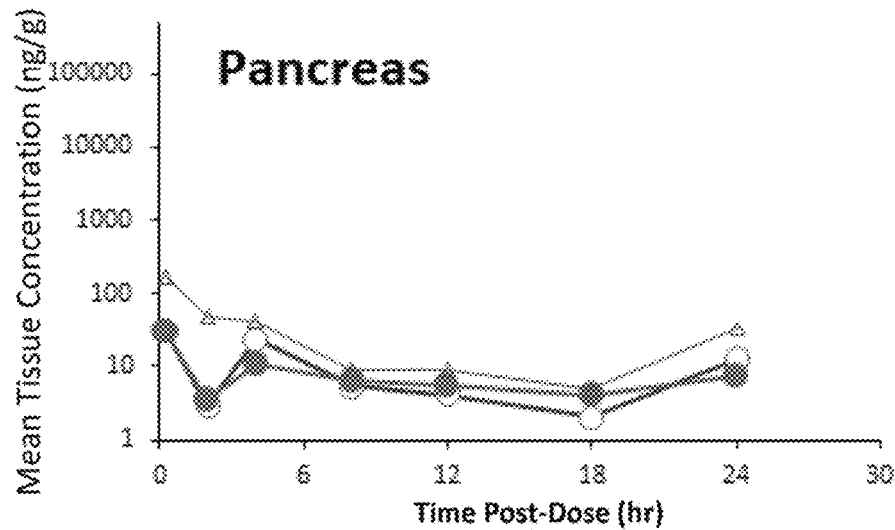
Figure 6C:
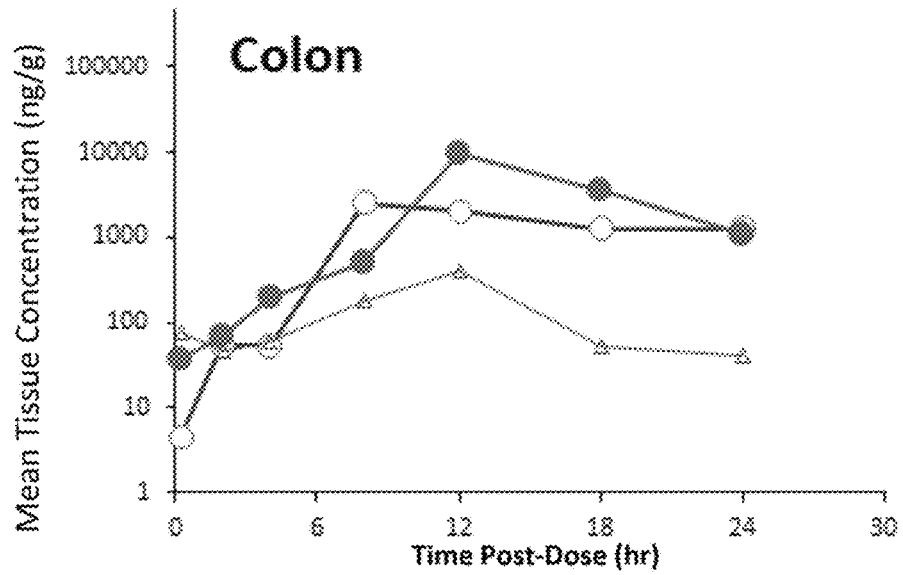

Drug Distribution in Selected Tissues:

Table 18 and FIGS. 6A-C show drug distribution in liver, pancreas, and colon.

TABLE 18

| | $T_{max}$ | $C_{max}$ | C24 | $AUC_{0-t}$ | $AUC_{0-\infty}$ | $t_{1/2}$ |
|---|---|---|---|---|---|---|
| Formula A | | | | | | |
| Plasma | 2.0 | 2 | <0.1 | 8 | 8 | 3.5 |
| Liver | 0.25 | 16 | 1.5 | 78 | 97 | 9.3 |
| Pancreas | 0.25 | 6 | 2.5 | 40 | 62 | 5.8 |
| Colon | 12.0 | 507 | 249 | 6320 | 12586 | 17.5 |
| Formula C | | | | | | |
| Plasma | 0.25 | 1 | 0.1 | 8 | 9 | 4.6 |
| Liver | 0.25 | 10 | 1.3 | 73 | 116 | 22.8 |
| Pancreas | 0.25 | 6 | 1.4 | 33 | 61 | 13.4 |
| Colon | 12.0 | 2002 | 218 | 15578 | 16762 | 3.8 |
| CPT-11* | | | | | | |
| Plasma | 0.25 | 60 | <0.1 | 105 | 105 | 4.2 |
| Liver | 0.25 | 29 | <0.1 | 113 | 113 | 2.5 |
| Pancreas | 0.25 | 10 | 0.4 | 36 | 56 | 6.9 |
| Colon | 12.0 | 25 | 0.5 | 216 | 228 | 3.5 |

*Normalized to Human Exposure (i.e., 5% conversion to SN-38 in human vs. 83.7% in rat).

For Formula A, $AUC_{0-24}$ of SN-38 in colon is 6320, much greater than that from CPT-11 (216) by 29.3-fold. Similarly for Formula C, $AUC_{0-24}$ of SN-38 in colon is 15578, ~72-fold greater than that from CPT-11 (216).

The results indicate that compared with CPT-11 IV dose, the oral SN-39 Formulations delivered >30-fold higher tissue concentrations of SN-38 in colon, ensured the sufficient drug exposure for treating the colorectal cancer.

The oral SN-38 Formulations provides sustain-released SN-38 levels in these tissues, suggesting a favorable PK profile of oral dose in cancer patients.

No CPT-11 exposure and ~10-30 fold less SN-38 plasma levels from oral SN-38 Formulations, as compared with CPT-11 IV dose, ensure a superior safety in much less systemic side effects.

The oral SN-38 Formulations delivered comparable SN-38 (AUC) in liver and pancreas than CPT-11 IV dose, and thus become potentially useful in treating tumor in liver/pancreas.

These animal PK studies demonstrated that the selected oral SN-38 formulations provide sufficient SN-38 to the targeted tumor tissues, e.g., liver and colon, etc., with long half-life (T½), and result in sustained-release profile in plasma and targeted tissues. In conclusion, the following two candidate formulations containing ~15 mg/g solubility of SN-38 were selected for animal pharmacological (efficacy) studies in xenograft model after evaluation from the results of animal PK studies:

1) Formula A: SN-38 in NMP:VitE TPGS:KOLLIDON® VA64 (50:20:20, w/w)
2) Formula C: SN-38 in NMP:VitE TPGS:HPC (50:20:5, w/w)

(C) Animal Pharmacological (Efficacy) Studies

Based on previous solubility tests and pharmacokinetic evaluation, the selected oral formulations of SN-38 were selected for further evaluated in human-like tumor (e.g., HCT-116 colon cancer cells) orthotopic xenograft mouse model with specified dosing regimen to demonstrate the desired anti-tumor activity. Following the scheduled repeated administration via oral route (p.o.), the pharmacological effects of each individual oral SN-38 formulations were determined by the Tumor Growth Inhibition (TGI %), compared with the intravenous (i.v.) or intraperitoneal (i.p.) injection of Irinotecan as a positive control.

Study #1—Advanced Analyses for Evaluation of the Efficacy of TRX-920 Formulations Orally Administered as Single Agents Using an Orthotopic HCT-116 Xenograft Model.

Formula A and Formula C were evaluated in orthotopic human colon cancer xenograft mouse model to demonstrate their pharmacologic effects. In these studies, both Formulation A and C were shown to be pharmacologically active, where Formula C was more effective than Formula A. Overall, the oral formulation of SN-38 was shown to be effective in treating colon cancer as demonstrated in orthotopic HCT-116 human colon cancer cell mouse xenograft model. The experimental design and results are summarized in the following tables:

(1) Study Design:

TABLE 19

| Group | Treatment | Route | Dose (mg/kg) | Dosing volume (µL/g) | Dosing schedule | No. of animal |
|---|---|---|---|---|---|---|
| 1 | Control (no treatment) | — | — | — | — | 10 |
| 2 | Formula A-H | p.o. | 12.0 | 5 | BIW x 3 wks | 10 |
| 3 | Formula A-L | p.o. | 2.4 | 5 | BIW x 3 wks | 10 |
| 4 | Formula C-H | p.o. | 12.0 | 5 | BIW x 3 wks | 10 |

TABLE 19-continued

| Group | Treatment | Route | Dose (mg/kg) | Dosing volume (µL/g) | Dosing schedule | No. of animal |
|---|---|---|---|---|---|---|
| 5 | Formula C-L | p.o. | 2.4 | 5 | BIW x 3 wks | 10 |
| 6 | Irinotecan HCL Trihydrate | i.v. | 20.8 | 5 | BIW x 3 wks | 10 |
| 7 | Irinotecan | i.p. | 50 | 5 | Q4D x 3 wks | 10 |

Formula A-H and Formula A-L are Formula A in high and low dose levels; Formula C-H and Formula C-L are Formula C in high and low dose levels.
Drug treatment frequencies and times: BIW (biw or b.i.w.): every Day 1 and Day 4 in one week (twice a week); Q4D: once every 4 days.

(2) Results:

TABLE 20

| | Tumor weights on Day 34 | | Tumor volume on Day 34 | |
|---|---|---|---|---|
| Groups | Geometric mean (mg) | TGI % | Geometric mean (mm³) | TGI % |
| Group-1 (control) | 781.0 | — | 752.6 | — |
| Formula A-H | 927.4 | −19 | 807.8 | −7 |
| Formula A-L | 650.7 | 17 | 493.1 | 34 |
| Formula C-H | 653.6 | 16 | 509.0 | 32 |
| Formula C-L | 655.4 | 16 | 518.1 | 31 |
| Irinotecan HCL trihydrate | 171.0 | 78 | 132.0 | 82 |
| Irinotecan | 24.9 | 85 | 16.4 | 88 |

Results: A similar anti-tumor activity (16-17% and 31-34% of TGI for tumor weights and tumor volumes on Day 34) was observed when administration of Formula A at low dose of 2.4 mg/kg, and Formula C at both high and low dose of 12 and 2.4 mg/kg. Overall, both Formulation A and C were pharmacologically active, where Formula C was more effective than Formula A.

Study #2—Advanced Analyses for a Follow Up Study on Evaluation of the Efficacy of TRX-920 Orally Administered as Single Agents Using Orthotopic HCT-116 Xenograft Model in Female BALB/c Nude Mice.

A follow up study was conducted to further evaluate the oral SN-38 formulation (Formula C) with increase of the dosing frequency in the same xenograft mouse model. The experimental design and results are summarized in the following tables. Briefly, Formula C at the doses of 2.5, 7.5, and 15.0 mg/kg of SN-38 were orally dosed to the animals by QD×4 days, 4 days off, BIW×3 doses. Effects on the tumor growth inhibition (TGI %) were measured from the tumor weights and tumor volumes on Day 32, compared to the untreated control.

(1) Study Design:

TABLE 21

| Group | Treatment | Route | Dose (mg/kg) | Dosing volume (µL/g) | Dosing schedule | No. of animal |
|---|---|---|---|---|---|---|
| 1 | Control (no treatment) | — | — | — | — | 10 |
| 2 | Formula C-H | p.o. | 15.0 | 5 | QD x 4 days, 4 days off, BIW x 3 doses | 10 |
| 3 | Formula C-M | p.o. | 7.5 | 5 | | 10 |
| 4 | Formula C-L | p.o. | 2.5 | 5 | | 10 |

TABLE 21-continued

| Group | Treatment | Route | Dose (mg/kg) | Dosing volume (μL/g) | Dosing schedule | No. of animal |
|---|---|---|---|---|---|---|
| 5 | Irinotecan HCL Trihydrate | i.v. | 25.9 | 5 | BIW x 6 doses | 10 |

Formula C-H, Formula C-M and Formula C-L are Formula C in High, Medium and Low dose levels.
BIW: every Day 1 and Day 4 in one week; QD: once daily (every day).

(2) Results:

TABLE 22

| | Tumor weights on Day 32 | | Tumor volume on Day 32 | |
|---|---|---|---|---|
| Groups | Geometric mean (mg) | TGI % | Geometric mean (mm³) | TGI % |
| Group-1 (control) | 851.9 | — | 936.8 | — |
| Formula C-H | 694.6 | 18 | 793.2 | 7 |
| Formula C-M | 386.5 | 55 | 387.3 | 55 |
| Formula C-L | 429.5 | 50 | 349.8 | 59 |
| Irinotecan HCL Trihydrate | 134.0 | 84 | 111.8 | 87 |

The TGI % values were 7-18%, 55% and 50-59% for the Formula C-H, -M, and -L groups, respectively. Groups Formula C-M and -L showed comparable and significant anti-tumor effects, whereas Formula C-H resulted in less TGI %, probably compromised by the SN-38 inherent GI toxicity response after oral dose. This study, again, demonstrated the significant pharmacological effect of oral SN-38 formulation (e.g., Formula C in this study) on the well-established anti-tumor xenograft mouse model.

Study #3—In Vivo Efficacy of TRX-920 Administrated Orally Evaluated Using an Orthotropic HCT-116 Xenograft Mouse Model This study was conducted to determine the minimal effective dose of oral SN-38 formulation (i.e., Formula C or denoted as TRX-920 in this study) in the same xenograft mouse model. Briefly, Formula C was orally administered to the animals at the dose range of 0.09-7.5 mg/kg of SN-38 by BIW×3 weeks. Effects on the tumor growth inhibition (TGI %) were measured from the tumor weights and tumor volumes on Day 34, compared to the untreated control. The experimental design and results are summarized in Tables 23-24.

(1) Study Design (Formula C, denoted as TRX-920):

TABLE 23

| Group | Treatment | Route | Dose (mg/kg) | Dosing volume (μL/g) | Dosing schedule | No. of animal |
|---|---|---|---|---|---|---|
| 1 | Control (no treatment) | — | — | — | — | 10 |
| 2 | TRX-920_7.5 | p.o. | 7.5 | 5 | BIW x 3 wks | 10 |
| 3 | TRX-920_2.5 | p.o. | 2.5 | 5 | BIW x 3 wks | 10 |
| 4 | TRX-920_0.8 | p.o. | 0.8 | 5 | BIW x 3 wks | 10 |
| 5 | TRX-920_0.27 | p.o. | 0.27 | 5 | BIW x 3 wks | 10 |
| 6 | TRX-920_0.09 | p.o. | 0.09 | 5 | BIW x 3 wks | 10 |
| 7 | Irinotecan HCL Trihydrate | i.v. | 25.9 | 5 | Q4D x 3 wks | 10 |
| Satellite | — | — | — | — | — | 3 |

(2) Results:

TABLE 24

| | Tumor weights on Day 34 | | Tumor volume on Day 34 | |
|---|---|---|---|---|
| Groups | Geometric mean (mg) | TGI % | Geometric mean (mm³) | TGI % |
| Group-1 (control) | 1061.1 | — | 1026.1 | — |
| TRX-920_7.5 | 509.2 | 52 | 409.7 | 60 |
| TRX-920_2.5 | 660.5 | 38 | 658.5 | 36 |
| TRX-920_0.8 | 754.8 | 29 | 815.7 | 21 |
| TRX-920_0.27 | 922.8 | 13 | 897.4 | 13 |
| TRX-920_0.09 | 605.3 | 43 | 561.9 | 45 |
| Irinotecan HCL Trihydrate | 428.6 | 60 | 418.9 | 59 |

Formula C, denoted as TRX-920.

Figure 7A:
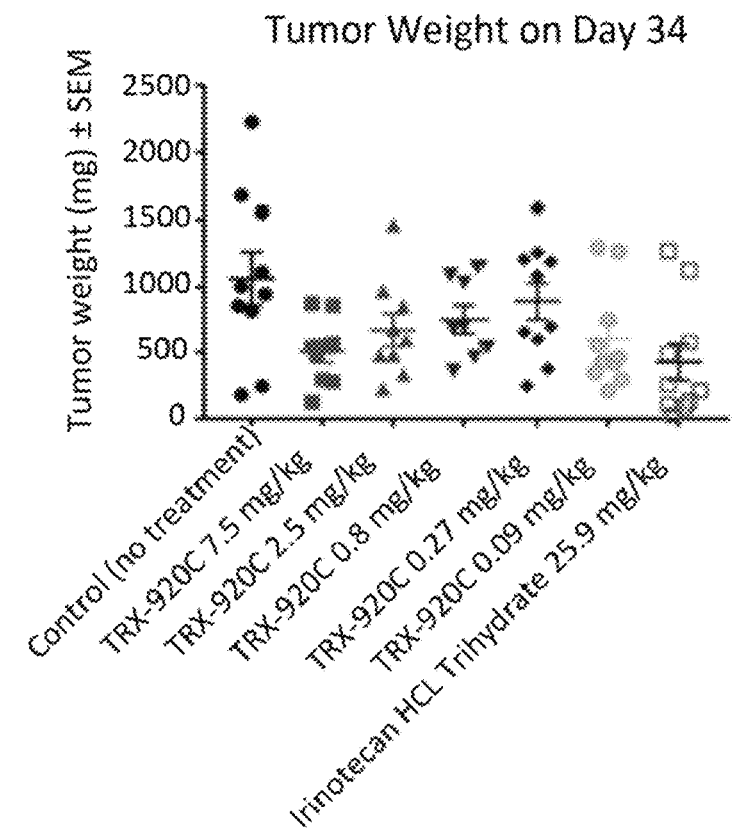
FIGS. 7A-B are dot plots showing tumor weight and tumor volume on Day 34 in control and experimental groups.
Figure 7B:
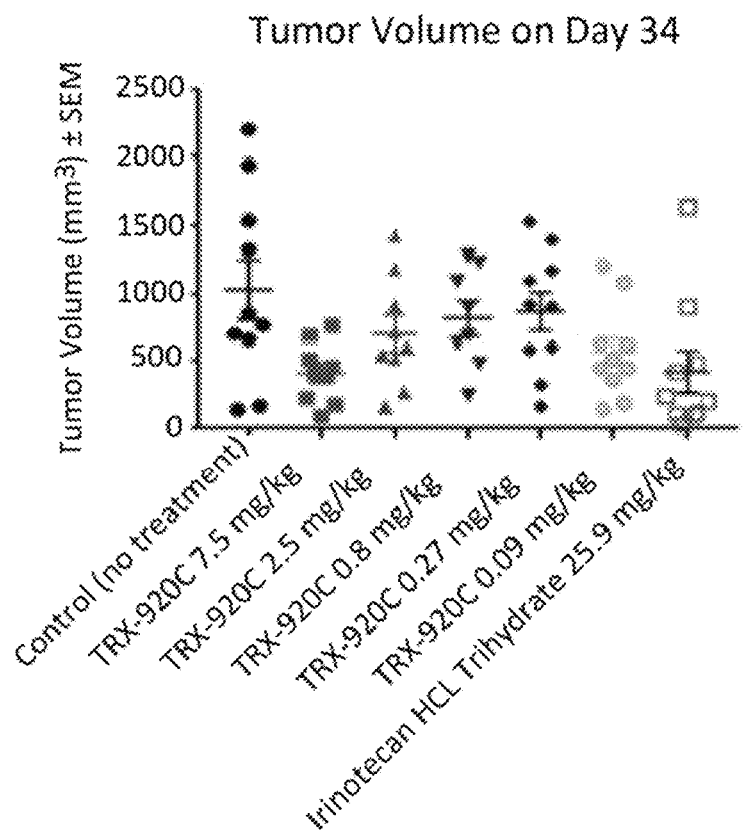

FIGS. 7A-B are dot plots showing tumor weight and tumor volume on Day 34 in each dosing group. Oral dose of Formula C at the range of 0.09-7.5 mg/kg by BIW×3 weeks were generally well tolerated in these xenograft animals. The study results showed a dose-proportional responses on reducing tumor size in the dose range of 0.27 mg/kg to 7.5 mg/kg, where Formula C at 7.5 mg/kg dose resulted in significant anti-tumor efficacy by TGI: 60.1% in tumor volume and 52.0% in tumor weight (p value $\leq 0.025$). Nevertheless, the lowest dose (0.09 mg/kg) also showed unexpected but good anti-tumor response (43-45%) in this disease model. Again, this dose-response study demonstrated the significant anti-tumor effect of oral SN-38 formulation (i.e., Formula C in this study) on the orthotopic HCT-116 xenograft mouse model.

In conclusion, all these 3 animal pharmacologic studies demonstrate that the oral SN-38 formulations, particularly Formula C, had significant anti-tumor effects in well-established orthotopic HCT-116 human colon cancer cell mouse xenograft model, therefore are potentially the novel oral formulation of SN-38 in treating patients with colorectal cancer.

All references cited and discussed in this specification are incorporated herein by reference in their entireties and to the same extent as if each reference was individually incorporated by reference.

What is claimed is:
1. A SN-38 formulated gel or solution, comprising:
   (a) N-Methylpyrrolidone (NMP);
   (b) Vitamin E TPGS (VitE TPGS) solubilized in NMP forming a VitE TPGS/NMP homogeneous medium;
   (c) 7-Ethyl-10-hydroxy-camptothecin (SN-38) solubilized in VitE TPGS/NMP homogeneous medium forming SN-38 in VitE TPGS/NMP solution (SN-38/VitE TPGS/NMP); and
   (d) a gelling/thickening polymer solubilized in SN-38/VitE TPGS/NMP forming a SN-38 formulated gel or solution without water and SN-38 precipitation, said gelling/thickening polymer being Hydroxypropyl cellulose (HPC), Hydroxypropyl methylcellulose (HPMC), or vinylpyrrolidone-vinyl acetate copolymer (VP/VAc copolymer 60/40), wherein NMP, VitE TPGS and the gelling/thickening polymer are at a weight ratio of:
   (i) NMP, VitE TPGS, and HPC from 50:20:1 to 50:20:5.0;
   (ii) NMP, VitE TPGS, and HPMC from 50:20:1 to 50:20:2.0; and
   (iii) NMP, VitE TPGS, and VP/VAc copolymer 60/40 of 50:20:20.0.

2. The SN-38 formulated gel or solution of claim 1, wherein
the gelling/thickening polymer is HPC or HPMC.

3. The SN-38 formulated gel or solution of claim 1, wherein
the weight ratio of NMP, VitE TPGS, and HPC is from 50:20:1 to 50:20:2.0.

4. The SN-38 formulated gel or solution of claim 1, wherein the weight ratio of NMP, VitE TPGS, and the polymer is from 50:20:2.5 to 50:20:5.0.

5. The SN-38 formulated gel or solution of claim 1, wherein the
gelling/thickening polymer is VP/Vac copolymer 60/40.

6. The SN-38 formulated gel or solution of claim 1, which is in an oral dosage form.

7. The SN-38 formulated gel or solution of claim 1, which is in capsule form or liquid-in-syringe form.

8. A method for treating a tumor, comprising:
administering the SN-38 formulated gel or solution of claim 1 in a therapeutically effective amount to a subject in need thereof for treating the tumor in the subject in need thereof, wherein the cancer tumor is at least one selected from the group consisting of liver, pancreatic, colon, ovarian, breast, gastric and colorectal tumor.

* * * * *